United States Patent [19]

Hofmann et al.

[11] Patent Number: 5,206,243
[45] Date of Patent: Apr. 27, 1993

[54] CONTROL OF FUNGAL INFECTIONS IN AQUACULTURE

[75] Inventors: Dieter Hofmann, Reinach; Walter Rehm, Riehen, both of Switzerland

[73] Assignee: Hoffmann-La Roche Inc., Nutley, N.J.

[21] Appl. No.: 666,833

[22] Filed: Mar. 8, 1991

[30] Foreign Application Priority Data

Mar. 12, 1990 [EP] European Pat. Off. ........ 90104627.6
Jan. 26, 1991 [EP] European Pat. Off. ........ 91101019.7

[51] Int. Cl.$^5$ .................. A61K 31/535; A61K 31/445
[52] U.S. Cl. .................................. 514/239.5; 514/317
[58] Field of Search .............................. 514/239.5, 315

[56] References Cited

U.S. PATENT DOCUMENTS

| | | | |
|---|---|---|---|
| 4,202,894 | 5/1980 | Pfiffner | 514/239.5 |
| 4,241,058 | 12/1980 | Pfiffner | 514/239.5 |
| 4,464,370 | 8/1984 | Gramlich et al. | 514/239.5 |

FOREIGN PATENT DOCUMENTS

| | | |
|---|---|---|
| 0024334 | 3/1981 | European Pat. Off. |
| 2822326 | 11/1979 | Fed. Rep. of Germany |
| 2056454 | 3/1981 | United Kingdom |

OTHER PUBLICATIONS

Chemical Abstracts (89:109522k) 1978.
Bohnen et al., Med. Fac. Landbouwn. Rijksuniv. Gent, 44/2, 487–497 (1979).
Polak et al., Recent Trends in the Discovery, Development and Evaluation of Antifungal Agents, 555-573 (1987).
Chemical Abstracts, 107, No. 5, 34963; (1987) Derwent Abstract of DE 2822326.
Tests Agrochem. Cultiv. 8, 66–67 (1987).

Primary Examiner—Frederick E. Waddell
Assistant Examiner—K. Weddington
Attorney, Agent, or Firm—George M. Gould; George W. Johnston; Stephen L. Malaska

[57] ABSTRACT

A method of controlling fungal infections of animals in aquaculture caused by the genus Fusarium spp. involves applying as a fungicidal or fungistatic agent a compound of formula

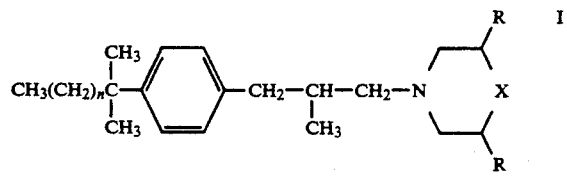

wherein n signifies 0 or 1 and either X signifies oxygen and R methyl or X signifies methylene and R hydrogen, or a salt thereof to the animals in aquaculture. The invention also concerns a fungicidal or fungistatic feed usable in such method.

16 Claims, No Drawings

CONTROL OF FUNGAL INFECTIONS IN AQUACULTURE

BACKGROUND OF THE INVENTION

The development of the commerical culture of animals in aquaculture, especially of crustacea, has been accompanied by the occurrence of infectious and noninfectious diseases. Many of the important diseases suffered by, for example, penaeid shrimps, are caused by organisms which are ubiquitous and have been established in all the major penaeid culture areas of the world, e.g. in Japan, Korea, Taiwan, the Philippines, Tahiti, Indonesia, Thailand, Malaysia, India, the Caribbean, Brazil, Mexico, Panama, Ecuador, Colombia, the U.S.A., Australia, France, Spain and Italy.

With increasing density and production level of penaeid shrimps diseases have broken out rapidly. Outbreaks of fungal infections, e.g. Lagenidium and Sirolpidium, bacterial attacks, e.g. Vibrio and Aeromonas, and even viruses, e.g. Baculovirus, are frequent in hatcheries, most of these problems being due to insufficient control of the rearing systems and absence of sanitary procedures as in terrestrial husbandry (disinfection, regular dry-out, separate equipment for each tank and separate rooms for maturation, spawning, hatching and larval rearing). The result is a weakening of the larvae and a lowering of their resistance to disease. Although antifungal agents such as trifluralin and Malachite green, and antibiotics used sparingly in the tanks have achieved some success the need to have a dry-out every six to eight weeks of production in order to eliminate bacterial strains which have become increasingly resistant and pathogenic has not been avoided.

SUMMARY OF THE INVENTION

It has now been found that compounds of the formula

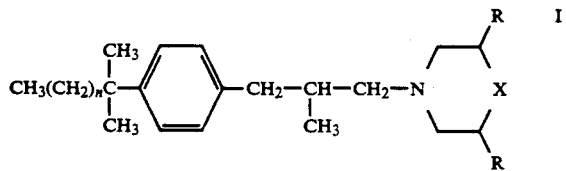

wherein n signifies 0 or 1 and X signifies oxygen and R methyl, or X signifies methylene and R hydrogen, and salts thereof are effective in controlling fungal infections of animals in aquaculture caused by the genus Fusarium spp. either by reducing or eradicating an existing infection or preventing it breaking out (fungicidal activity) or by preventing the spreading of an existing infection (fungistatic activity). Accordingly, the present invention provides a method of controlling fungal infections of animals in aquaculture caused by the genus Fusarium spp., characterized by applying as a fungicidal or fungistatic agent a compound of the formula I given above or a salt thereof to the animals in aquaculture.

DETAILED DESCRIPTION OF THE INVENTION

The present invention concerns a compound of the formula

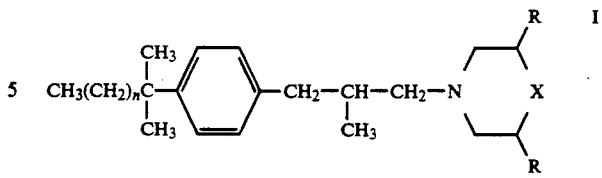

wherein n is 0 or 1 and X is oxygen and R methyl, or X is methylene and R hydrogen, and salts thereof, its racemates and isomers.

These compounds are effective in controlling fungal infections of animals in aquaculture caused by the genus Fusarium spp. either by reducing or eradicating an existing infection or preventing it breaking out (fungicidal activity) or by preventing the spreading of an existing infection (fungistatic activity). Accordingly, the present invention provides a method of controlling fungal infections of animals in aquaculture caused by the genus Fusarium spp., characterized by applying as a fungicidal or fungistatic agent a compound of the formula I given above or a salt thereof to the animals in aquaculture.

In view of the presence of an asymmetric carbon atom in the compounds of formula I, the compounds occur in optically active form. The representation of formula I is accordingly intended to embrace the racemates as well as the separated optically active isomers. Moreover, the opportunity for a cis- and a trans-arrangement of the methyl substituents of the morpholine ring (in the case when X signifies oxygen) is encountered, giving rise to geometrical isomerism, and formula I is accordingly intended to embrace the separated geometrical isomeric forms (cis- and trans-forms) as well as mixtures thereof.

Salt formation of the compounds of formula I is rendered possible by virtue of the basic nature of the nitrogen atom of the morpholine or piperidine ring. The salts of the compounds I contemplated are those with physiologically acceptable acids, in particular hydrohalic acids, e.g. hydrochloric acid and hydrobromic acid; phosphoric acid; nitric acid; monofunctional and bifunctional carboxylic acids and hydroxycarboxylic acids, e.g. acetic acid, maleic acid, succinic acid, fumaric acid, tartaric acid, citric acid, salicylic acid, sorbic acid and lactic acid; and sulphonic acids, e.g. 1,5-naphthalene-disulphonic acid.

The compounds of formula I and their salts, as well as the use of these substances as fungicidal and fungistatic agents in the control of fungi pathogenic to plants, animals and humans, are described in the patent and scientific literature, e.g. in U.S. Pat. Nos. 4,202,894 and 4,241,058 (Bohnen and Pfiffner), European Patent Specification No. 24,334 (Pfiffner), Med. Fac. Landbouww. Rijksuniv. Gent, 44/2, pages 487-497 (1979; Bohnen and Pfiffner), and "Antifungal Activity of Amorolfine (Ro 14-4767/002) in vitro and in vivo" by Polak and Dixon, Recent Trends in the Discovery, Development and Evaluation of Antifungal Agents, R.A. Fromtling (Ed.), pages 555-573 (1987, J. R. Prous Science Publishers, S.A.).

In the last-mentioned article the in vitro fungistatic activity of amorolfine [INN, published as recommended by the WHO; hydrochloride salt of the cis-compound of formula I in which n is 1, X is oxygen and R is methyl] on various medically important fungi is reported. On the basis of the results given, inter alia, the poor or non-existent activity against opportunistic mold such as Fusarium spp. (see Table 1 on page 561), the present finding of the excellent activity of the compounds of formula I in the control of fungi of the genus Fusarium spp. in aquaculture must be deemed to be very surprising.

Of the compounds of formula I and their salts the previously mentioned amorolfine (rac-cis-4-{3-[4-(1,1-dimethylpropyl)-phenyl]-2-methyl-propyl}-2,6-dimethylmorpholine hydrochloride), and particularly cis-4-[3-(4-tert.butylphenyl)-2-methyl-propyl]-2,6-dimethylmorpholine (fenpropimorph, Corbel®), have been found to be especially suitable fungicidal or fungistatic agents in the method of the present invention. A further especially suitable compound of formula I is (RS)-1-[3-(4-tert.butylphenyl)-2-methyl-propyl]-piperidine (fenpropidin).

In practice the compound of formula I or salt thereof is applied to the animals in their aqueous environment, e.g. tank or pond, undiluted or in association with inert solid or liquid diluting medium. Such inert solid or liquid diluting medium may take the form essentially of water, in which case the compound of formula I or salt thereof is conveniently dissolved or otherwise dispersed therein, if necessary with the aid of wetting, emulsifying and/or dispersing agents. In particular, however, the inert solid or liquid diluting medium may consist of feed for fish or crustacea, and in such medicated feeds the content of active ingredient, i.e. compound of formula I or salt thereof, is generally in the range about 0.0001 to about 0.1 percent by weight, preferably about 0.003 to about 0.01 percent by weight. Such a medicated feed for fish or crustacea is preferably in the form of pellets or microcapsules.

The rate at which the compound of formula I or a salt thereof is applied to the aquatic environment of the animals to be treated is generally in the range about 1 to about 50 $\mu$g/l, preferably in the range about 10 to about 25 $\mu$g/l. By aquatic environment is meant the water, e.g. sea or fresh water, contained in a tank, pond, etc. in which the animals to be treated are maintained.

The type of animals in aquaculture to be treated against fungal infectious caused by Fusarium spp. is preferably crustacea. This class of aquatic animals embraces inter alia members of the genus Penaeids (Penaeus spp.), fresh water prawns (Macrobrachium spp.) and lobsters (Homarus spp.), and such species are particularly effectively treated according to the method of the present invention. More particularly, the Penaeus spp. treated according to the method of the present invention are warm water or cold water shrimps, such as *Penaeus (P.) aztecus, P. brasiliensis, P. brevirostris, P. californiensis, P. canaliculatus, P. caramote, P. carinatus, P. duorarum, P. esculentus, P. indicus, P. japonicus, P. kerathurus, P. latisulcatus, P. merguiensis, P. monodon, P. occidentalis, P. orientalis, P. plebejus, P. schmitti, P. semisulcatus, P. setiferus, P. sinensis, P. stylirostris, P. trisulcatus, P. vannamei, Metapenaeus (M.) ensis* and *M. monoceros*. In the case of fresh water prawns the method of the present invention is preferably directed to the control of fungal infections of *Macrobrachium (M.) carcinus, M. nipponense* and *M. rosenbergii*, and in the treatment of lobsters those preferably treated are of the species *Homarus (H.) americanus, H. gammarus* and *H. vulgaris*.

The method of the present invention can be applied for a curative or preventive purpose, but the control is preferably curative.

Moreover, although the method of the present invention can be utilized for the control of fungal infections in any development stage (e.g. egg, larval or post-larval stage) of the animals in aquaculture to be treated, it is preferably effected for the control of a fungal infection in the post-larval development stage of said animals. By larval development stage is meant the growth stage in which the animals to be treated are in the form of larvae (see in this connection the articles "A Brief Review of the Larval Rearing Techniques of Penaeid Prawns" and "Overview of Penaeid Culture Research: Impact on Commercial Culture Activity" in Proceedings of the First International Conference on the Culture of Penaeid Prawns/Shrimps, Iloilo City, Philippines 1984, pages 1–10 and 65–78, respectively (© 1985 SEAFDEC Aquaculture Department).

The method according to the invention is preferably applied for controlling fungal infections caused by *Fusarium solani*.

In principle the method can be carried out in any type of aquaculture, but is particularly effected in a hatchery, a growing pond, a nursery pond or a rearing pond. Furthermore, the frequency with which the treatment (i.e. the applications of the compound of formula I or a salt thereof to the animals in aquaculture) is effected can be varied according to the experience gained by observing the results, but in general, and conveniently, the method is carried out at regular intervals, preferably every two to four weeks.

The present invention also provides a fungicidal or fungistatic feed for fish or crustacea, characterized in that it is intended for the control of fungal infections caused by the genus Fusarium spp. in aquaculture and contains as a fungicidal or fungistatic agent an effective amount of at least one compound of formula I, as given above, or a salt thereof.

In such a medicated feed for fish or crustacea the percentage weight content of active ingredient will depend on the volume of the aqueous environment in which the fish or crustacea find themselves (e.g. tank or pond water), and the desired final concentration of the compound of formula I or salt thereof in said aqueous environment. For practical purposes the content of active ingredient in the fungicidal or fungistatic feed is generally in the range about 0.0001 to about 0.1 percent by weight. The preferred range is about 0.003 to about 0.01 percent by weight. The feed is preferably in the form of pellets or microcapsules.

The present invention further provides the use of a compound of the formula I, as given above, or a salt thereof for controlling fungal infections of animals in aquaculture caused by the genus Fusarium spp.

The invention is illustrated by the following examples. Unless indicated otherwise, the examples were carried out as written.

EXAMPLE 1

In vitro Evaluation of the Fungicidal/Fungistatic Activity of cis-4-[3-(4-Tert.butyl-phenyl)-2-methyl-propyl]-2,6-dimethylmorpholine (fenpropimorph) against *Fusarium solani*

1. Isolation of *Fusarium solani*

The strain of *Fusarium (F.) solani* used in the tests was isolated from a shrimp of the species Penaeus japonicus affected with *F. solani*, i.e. suffering from an infection caused by Fusarium spp. The mould was cultured at 22°

C. on agar [DST Agar (Oxoid)] to which brine had been added to the extent 20 g NaCl/l.

2. Tests for antifungal activity on mycelium and conidiospores a) Preparation of the antifungal solutions: The initial "mother solution" of concentration 200×μl/l was prepared by transferring 2×μl of fenpropimorph into 1 ml of Tween ® 20 (emulsifying agent by Atlas Powder Co, Wilmington, Del.; polyethoxysorbitane laurate) to which dimethyl sulphoxide had been added up to a total volume of 10 ml. This mother solution was submitted to a first dilution (1→2 volumes) with a further quantity of Tween ® 20 (0.5 ml)/dimethyl sulphoxide. The range of concentrations investigated was obtained by successive dilutions (initially 1→100 volumes and subsequently 1→2 volumes) of the mother solution with filtered autoclaved sea water. The mean salinity and pH of this sea water was 32‰ and 8, respectively.

b) Preparation of the inoculum: The inoculum consisted of a portion of the aforementioned agar taken from the surface and containing *F. solani* in a Petri dish (φ 9 cm). The inoculum is removed at the periphery of the culture of *F. solani* aged for one week. The microscopic examination of this inoculum confirmed *F. solani* in the form of mycelium and conidiospores.

c) Test procedure: For each concentration of fenpropimorph in the solution to be tested the inoculum was placed into 5 ml of the antifungal solution. After a 24 hours incubation period at 22° C. three rinsings of the inoculum were carried out with filtered autoclaved sea water. The inoculum was then placed at the centre of a Petri dish (φ 9 cm; volume of agar DST Agar 10 ml) and the whole incubated at 22° C. until the evaluation.

3. Determination of the Results

The in vitro activity of fenpropimorph on mycelium and conidiospores of *F. solani* was estimated 15 days after termination of the 24 hours treatment by calculating an index of growth inhibition, expressed as a percentage activity.

4. Results

These are presented in the following table:

| | Percentage activity | |
|---|---|---|
| Concentration of fenpropimorph in μl/l | Test 1 (average total surface area of control cultures 40.4 cm²) | Test 2 (average total surface area of control cultures 37.2 cm²) |
| 3.125 | 83.5 | 85.5 |
| 6.25 | 96 | 96.5 |
| 12.5 | 100 | 100 |
| 25 | 100 | 100 |
| 50 | 100 | 100 |

5. Conclusions from the in vitro study

The activity of fenpropimorph remains very high even at the lower concentrations tested. On the basis of a "fungicidal" activity fenpropimorph displays a fungicidal activity at concentrations greater or equal to 12.5 μl/l on *F. solani*. At lower concentrations the activity may be considered to be fungistatic. However, despite the absence of regrowth measurable 15 days after the antifungal treatment the inoculum seems to survive on application of antifungal solutions of concentrations 12.5 and 25 μl fenpropimorph/l in view of the appearance of some off-white points of regrowth. Consequently, a strictly fungicidal activity is realized at concentrations above 25 μl fenpropimorph/l.

What is indicated above for activity on mycelium and conidiospores is also valid for activity on conidiospores of *F. solani* alone. On non-germinated conidiospores of *F. solani* the strictly fungicidally effective concentrations of fenpropimorph are from 15 μl/l. On germinated conidiospores, (i.e. "young" mycelium), the activity of fenpropimorph is considerably higher.

EXAMPLE 2

In vitro Evaluation of the Fungicidal/Fungistatic Activity of rac-cis-4-{3-[4-(1,1-Dimethylpropyl)-phenyl]-2-methylpropyl}-2,6-dimethylmorpholine hydrochloride (amorolfine) against *Fusarium solani*

*Fusarium solani* was isolated and cultured as described in part 1 of Example 1. Analogous to the method described in part 2a) of Example 1, antifungal solutions of amorolfine were prepared, starting from a mother solution of concentration 100×mg/l and finishing with solutions in sea water of concentrations ×, ×/2, ×/4 etc. mg/l.

300 μl of agar (DST Agar) to which had been added 20 g/l of sodium chloride were added to the base of each of a series of 5 ml test tubes. In each case the agar was then cultured with 10 μl of a suspension of conidiospores of *Fusarium solani*, titrating about $5\times10^5$ conidiospores/ml. After 4 days incubation at 22° C. in such a way that the mycelium could occupy the whole surface of the agar and produce conidiospores 3 ml of antifungal solution of known concentration were transferred into each tube. After 24 hours incubation at 22° C. three drainings and 2 rinsings with filtered autoclaved sea water are effected. The third rinsing was followed by one of two procedures:

in the procedure *without* subculturing 3 ml of Sabouraud bouillon (a special nutrient medium for the culturing of Fusarium spp.) were added to each tube;

in the procedure *with* subculturing a withdrawal of mycelium and conidiospores is effected on the surface of the agar in each tube. Each inoculum so withdrawn, not quantified precisely, was deposited in a fresh tube at the surface of 300 μl of agar.

The evaluation of the tests was effected 15 days after the 24 hours treatment. In the procedure without subculturing the activity was qualified as truly fungicidal and denoted with "+" if no regrowth of fungus could be detected in the macroscopic examination of the agar. The activity was deemed to be of a fungistatic nature and denoted with "±" if regrowth of the fungus could be detected, albeit less rapid than that of the non-treated fungus in the control tubes. In the case of there being no difference between the regrowth of the treated and untreated (control) fungus this was denoted "−". In the procedure with subculturing any antifungal activity was denoted "+" in the case of the absence of macroscopically detectable regrowth and denoted "−" for the opposite situation. The results are presented in the following table:

| Concentration of amorolfine in mg/l (x = 160) | 0 | 1.25 | 2.5 | 5 | 10 | 20 | 40 | 80 | 160 |
|---|---|---|---|---|---|---|---|---|---|
| Fungicidal/fungistatic activity (procedure | + | ± | ± | ± | + | + | + | + | + |

| | |
|---|---|
| without subculturing) | |
| Fungicidal/fungistatic activity (procedure with subculturing) | − − − − − + + + + |

The conclusions drawn were that in the procedure without subculturing the minimum concentration of amorolfine in the aqueous medium which allowed in vitro an activity of fungicidal nature lay between 5 and 10 mg/l, whereas in the procedure with subculturing, which perhaps eliminated a residual antifungal effect due to the accumulation of product in the agar not eliminated in the rinsings this minimum fungicidal concentration was higher and lay between 10 and 20 mg/l.

EXAMPLE 3

In vitro Evaluation of the Fungicidal/Fungistatic Activity of (RS)-1-[3-(4-Tert.butyl-phenyl)-2-methyl-propyl]-piperidin (fenpropidin) against *Fusarium solani*

*Fusarium solani* was isolated and tests for antifungal activity on mycelium and conidiospores and the determination of the results were carried out for fenpropidin by analogous procedures to those described in Example 1 hereinbefore for fenpropimorph. The appropriate results are presented in the following table:

| | Percentage activity | |
|---|---|---|
| Concentration of fenpropidin in μl/l | Test 1 (average total surface area of control cultures 40.4 cm$^2$) | Test 2 (average total surface area of control cultures 37.2 cm$^2$) |
| 6.25 | 84 | 86 |
| 12.5 | 95 | 94 |
| 25 | 100 | 100 |
| 50 | 100 | 100 |

Conclusions from the in vitro study

The activity of fenpropidin remains very high even at the lower concentrations tested. On the basis of a "fungicidal" activity fenpropidin displays a fungicidal activity at concentrations greater or equal to 25 μl/l on *F. solani*. At lower concentrations the activity may be considered to be fungistatic. However, inspite of the absence of regrowth measurable 15 days after the antifungal treatment the inoculum seems to survive on application of antifungal solutions of concentrations 25 and 50 μl fenpropidin/l in view of the appearance of some off-white points of regrowth. Consequently, a strictly fungicidal activity is realized at concentrations above ca. 25 μl fenpropidin/l.

What is indicated above for activity on mycelium and conidiospores is also valid for activity on conidiospores of *F. solani* alone. On non-germinated conidiospores of *F. solani* the strictly fungicidally effective concentrations of fenpropidin are from 25 μl/l. On germinated conidiospores (i.e. "young" mycelium) the activity of fenpropidin is considerably higher.

EXAMPLE 4

In a shrimp farm the shrimps are maintained in an extensive or intensive manner and in both cases are fed during the growing phase 2 or 3 times a day, depending on their growth stage and weight. The shrimps eat slowly and more or less continuously. Shrimps which are in the growth stage of just a few days after the attainment of post-larval stage or those weighing 2–5 g require a different amount of feed compared with shrimps weighing 10 g or more, and in addition the pellet diameter of pelleted feed must also be chosen according to the growth stage or weight of the shrimps to be fed therewith. Thus, for a shrimp weighing 0.5–2 g a pellet diameter of 1–2 mm is usually acceptable, whereas a pellet diameter of 3–5 mm is generally recommended for shrimps weighing 10 g or more.

A typical shrimp feed in pelleted form with a pellet diameter appropriate for the growth stage or size of shrimps to be fed to shrimps in intensive culture has the following composition:

| | Percent by weight |
|---|---|
| Fish meal | 16 |
| Shrimp head meal | 15 |
| Squid meal | 5 |
| Soybean meal | 31 |
| Cereal products or by-products | 22–24 |
| Fish oil | 4 |
| Soybean lecithin | 1 |
| Cholesterol | 0.2 |
| Binder | 1–3 |
| Dicalcium phosphate | 2.25 |
| Vitamin mix | 0.5 |
| Trace mineral mix | 0.05 |
| | 100 |

The pelleted feed is administered by hand or automatic feeder. Shrimps in the post-larval stage normally require an amount of feed which is approximately 25–50% of their body weight 2 or 3 times a day. This amount may be decreased to about 3% for shrimps in extensive culture. The most effective way to determine the amount of feed necessary is to feed the shrimps according to their demand. This is accomplished by placing sufficient feed in a feeding tray or on a feeding platform, checking the amount remaining, if any, a few hours thereafter, and decreasing or increasing the next amount of feed appropriately. The required daily feed allowance is also indicated by the activity and behavior of the shrimps. For example, underfeeding is indicated if one or two hours after feeding a significant number of shrimps tend to remain at the edge of the pond or tank.

For the treatment of fungal infections caused by Fusarium spp. the feed composition given above was augmented with 0.0001–0.1%, preferably 0.003–0.01% by weight of a compound of the formula I hereinabove or a salt thereof, e.g. cis-4-[3-(4-tert.butyl-phenyl)-2-methyl-propyl]-2,6-dimethylmorpholine (fenpropimorph), rac-cis-4-{3-[4-(1,1-dimethylpropyl)-phenyl]-2-methyl-propyl}-2,6-dimethylmorpholine hydrochloride (amorolfine) or (RS)-1-[3-(4-tert.butyl-phenyl)-2-methyl-propyl]-piperidin (fenpropidin). An amount of such medicated feed was administered once or twice during a day according to the demand of the shrimps, and this was repeated after three weeks, and once again after a further three weeks.

It was consequently established that shrimps provided with such medicated feed remained substantially free of fungal infections caused by Fusarium spp.

We claim:

1. A method for controlling a fungal infection in fish and crustacea caused by the genus Fusarium spp., comprising applying to the fish or crustacea a compound of the formula

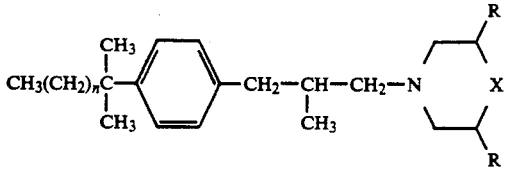

wherein n is 0 or 1 and X is oxygen and R methyl, or X is methylene and R hydrogen, or a salt thereof, its racemates, and isomers, in an amount which is effective as a fungicidal or fungistatic agent.

2. The method according to claim 1, wherein in compound I, X is oxygen and R methyl.

3. The method according to claim 2, wherein compound I is cis-4-[3-(4-tert.butyl-phenyl)-2-methylpropyl]-2,6-dimethylmorpholine.

4. The method according to claim 1, comprising applying compound I or salt thereof in undiluted form.

5. The method according to claim 1, comprising adding an inert solid or liquid diluting medium with compound I or salt thereof to form a composition.

6. The method according to claim 5, comprising preparing the composition such that the diluting medium is feed for fish or crustacea, and the concentration of compound I or salt thereof is in the range of about 0.003 to about 0.01 percent by weight of the composition.

7. The method according to claim 1, comprising applying compound I or salt thereof at a rate of from about 1 to about 50 μg/l of aquatic environment of the fish and crustacea.

8. The method according to claim 1, wherein the crustacea are members of the genus Penaeids (Penaeus spp.), fresh water prawns (Macrobrachium spp.) or lobsters (Homarus spp.).

9. The method according to claim 8, wherein the crustacea are warm water or cold water shrimps of the species *Penaeus (P.) aztecus, P. brasiliensis, P. brevirostris, P. californiensis, P. canaliculatus, P. caramote, P. carinatus, P. duorarum, P. esculentus, P. indicus, P. japonicus, P. kerathurus, P. latisulcatus, P. merguiensis, P. monodon, P. occidentalis, P. orientalis, P. plebejus, P. schmitti, P. semisulcatus, P. setiferus, P. sinensis, P. stylirostris, P. trisulcatus, P. vannamei, Metapenaeus (M.) ensis* or *M. monoceros*.

10. The method according to claim 8, wherein the crustacea are fresh water prawns of the species *Macrobrachium (M.) carcinus, M. nipponense* or *M. rosenbergii*.

11. The method according to claim 8, wherein the crustacea are lobsters of the species *Homarus (H.) americanus, H. gammarus* or *H. vulgaris*.

12. The method according to claim 1, wherein the method is for treating the fish and crustacea afflicted with such fungal infection.

13. The method according to claim 1, comprising controling the fungal infection during a post-larval development stage of the fish and crustacea.

14. The method according to claim 1, wherein the species of fungus causative of the fungal infection to be controlled is *Fusarium solani*.

15. The method according to claim 1, comprising carrying out the method in a hatchery, a growing pond, a nursery pond, or a rearing pond.

16. The method according to claim 1, comprising carrying out the method at regular intervals about every two to four weeks.

* * * * *